United States Patent [19]

Hohne

[11] Patent Number: 4,866,265
[45] Date of Patent: Sep. 12, 1989

[54] OPTICAL MOISTURE SENSOR USING AN EXPANDED OPTICAL BEAM

[75] Inventor: Harold Hohne, Brooklyn, N.Y.

[73] Assignee: Nynex Corporation, New York, N.Y.

[21] Appl. No.: 166,568

[22] Filed: Mar. 11, 1988

[51] Int. Cl.$^4$ .......................... H01J 5/16; H01J 40/14
[52] U.S. Cl. ................................. 250/227; 250/231 R
[58] Field of Search ..................... 250/227, 577, 231 R; 356/133, 134, 135, 136, 137, 436; 73/293, 73; 455/610, 612; 350/96.15, 96.20

[56] References Cited

U.S. PATENT DOCUMENTS

| | | | |
|---|---|---|---|
| 4,221,962 | 9/1980 | Black et al. | 73/73 |
| 4,270,049 | 5/1981 | Tanaka et al. | 250/227 |
| 4,421,979 | 12/1983 | Asawa et al. | 250/227 |
| 4,443,699 | 4/1984 | Keller | 73/293 |
| 4,459,477 | 7/1984 | Asawa et al. | 250/227 |
| 4,634,856 | 1/1987 | Kirkham | 250/227 |
| 4,653,916 | 3/1987 | Henning et al. | 356/345 |
| 4,673,819 | 6/1987 | Rose | 250/577 |
| 4,676,587 | 6/1987 | Mori | 350/96.20 |
| 4,727,247 | 2/1988 | Johnston | 250/227 |

OTHER PUBLICATIONS

H. Swano et al., "Optical Fiber Cable with Submersion Sensor Fiber", International Wire and Cable Symposium Proceedings, 1987, pp. 284-289.

Kukita et al., "A New Nonmetallic and Waterproof Optical Fiber Cable with Absorbent Polymer Ribbon", International Wire and Cable Symposium Proceedings, 1987, pp. 357-371.

James Carroll et al., "Design Considerations of Expanded Bean Lamdek Single-Mode Connector", Lamdek Fiber Optics, Publication Part No. LFD-02.

Primary Examiner—David C. Nelms
Assistant Examiner—William L. Oen
Attorney, Agent, or Firm—Robin, Blecker & Daley

[57] ABSTRACT

An optical moisture sensor including a housing having a port for coupling with an optical beam and an optical means for receiving the optical beam and providing therefrom an expanded, collimated optical beam, the optical means further including moisture responsive means for affecting the expanded, collimated beam.

26 Claims, 3 Drawing Sheets

OPTICAL MOISTURE SENSOR USING AN EXPANDED OPTICAL BEAM

BACKGROUND OF THE INVENTION

This invention pertains to moisture sensors and, in particular, to moisture sensors utilizing optical techniques.

With the advent of optical fibers, assemblies which utilize such fibers in conjunction with optical techniques have been proposed for sensing the moisture condition of a location. U.S. Pat. No. 4,634,856 discloses a number of such fiber optic moisture sensing assemblies.

In one assembly disclosed in the '856 patent, a reflective target whose reflectance changes with moisture is situated at the end of an optical fiber and a light source, such as, for example, a laser generates light for coupling along the fiber to the target. By monitoring the light reflected from the target, an indication of the moisture content of the environment of the target can be ascertained.

In a second assembly described in the '856 patent, the optical fiber itself is adapted so that the light transmission properties of the fiber change with changes in moisture. Accordingly, by monitoring the change in light transmitted through the fiber, an indication of moisture conditions can be determined.

The '856 patent discloses various ways of adapting an optical fiber to make it moisture sensitive. One way is to select the fiber cladding from materials whose refractive index varies with moisture content. Another way is to induce imperfections in the fiber, such as splices or microscopic holes which will have different optical qualities depending upon their moisture content. Still another technique is to use two coupled fibers, with the amount of light coupled between fibers being a function of the moisture content of their cladding materials.

While the '856 patent describes general techniques for achieving fiber-optic moisture sensors, other fiber-optic moisture sensors have been proposed specifically for use with fiber optic communication or transmission lines. These sensors are disposed at closures along their respective transmission line and their fibers are adapted to undergo mechanical bending or distortion in response to moisture or water entry into the associated closure. In particular, the fibers are bent or distorted by elements which change dimension as a function of a change in water content. Moisture sensors of this type are disclosed, for example, in the following publications: "Optical Fiber Cable With Submersion Sensor Fiber", H. Sawano, et. al., International Wire and Cable Symposium Proceedings, 1987, pgs. 284–289; "A New Nonmetallic and Waterproof Optical Fiber Cable With Absorbent Polymer Ribbon, Kukita, et. al., International Wire and Cable Symposium Proceedings, 1987, pgs. 357–371.

The above moisture sensors designed for use with fiber-optic transmission lines have been developed to overcome certain disadvantages encountered in present day transmission systems. In particular, in systems in use today, so called "all filled" fiber cables are used for added moisture resistance. Additionally, at closure locations two closures are normally required. An inner closure houses the fiber cable, while an outer closure houses a water repellant encapsulation which surrounds the inner closure.

By using an appropriate moisture sensor at the closure locations, the aforesaid outer closure and encapsulation can be dispensed with. Furthermore, the fiber cable need no longer be an "all filled" cable. The result is that the size and cost of the closure and the cost of installation of the closure can be decreased. Also, the maintenance of the closure is made easier.

While the above advantages can thus be realized by using suitably designed optical moisture sensors at the closure locations of a fiber-optic transmission line, the sensors discussed above which rely on a changing the characteristics of the optical fiber itself with changes in moisture may not be entirely practical or easily realizeable. Accordingly, there still remains a need for an optical moisture sensor which can be readily realizeable from existing assemblies and which has a rapid response.

It is therefore a primary object of the present invention to provide an optical moisture sensor which can be readily realized and which is rapidly responding.

It is a further object of the present invention to provide an optical moisture sensor which is readily adaptable from existing assemblies.

It is yet a further object of the present invention to provide an optical moisture sensor which can be readily adapted for use in closures of a fiber optic transmission line.

SUMMARY OF THE INVENTION

In accordance with the principles of the present invention, the above and other objectives are realized in a moisture sensor in which a housing having a port for coupling with an optical beam is provided and in which the sensor further includes optical means for receiving the optical beam and providing therefrom an expanded, collimated optical beam. In further accord with the invention, the optical means further includes moisture responsive means for affecting the expanded, collimated beam. As a result, by sensing the beam (either directly or indirectly via a beam derived therefrom), it is possible to sense the moisture condition of the environment of the sensor.

In the embodiment of the invention to be disclosed hereinafter, the sensor housing has a second port and the optical means is further adapted to contract the expanded, collimated beam for coupling with the second port. Furthermore in this embodiment, first and second fiber-optic cables are provided at the first and second ports of the sensor for coupling optical beams therethrough.

In a further aspect of the present invention, the sensor of the invention is further adapted to monitor the moisture conditions at closures of a fiber-optic transmission line. In such case, the sensor at each closure is connected in-line with one of the fiber optic lines passing through the transmission system.

BRIEF DESCRIPTION OF THE DRAWINGS

The above and other features and aspects of the present invention will become more apparent upon reading the following detailed description in conjunction with the following drawings, in which.

DETAILED DESCRIPTION

Figure 1:
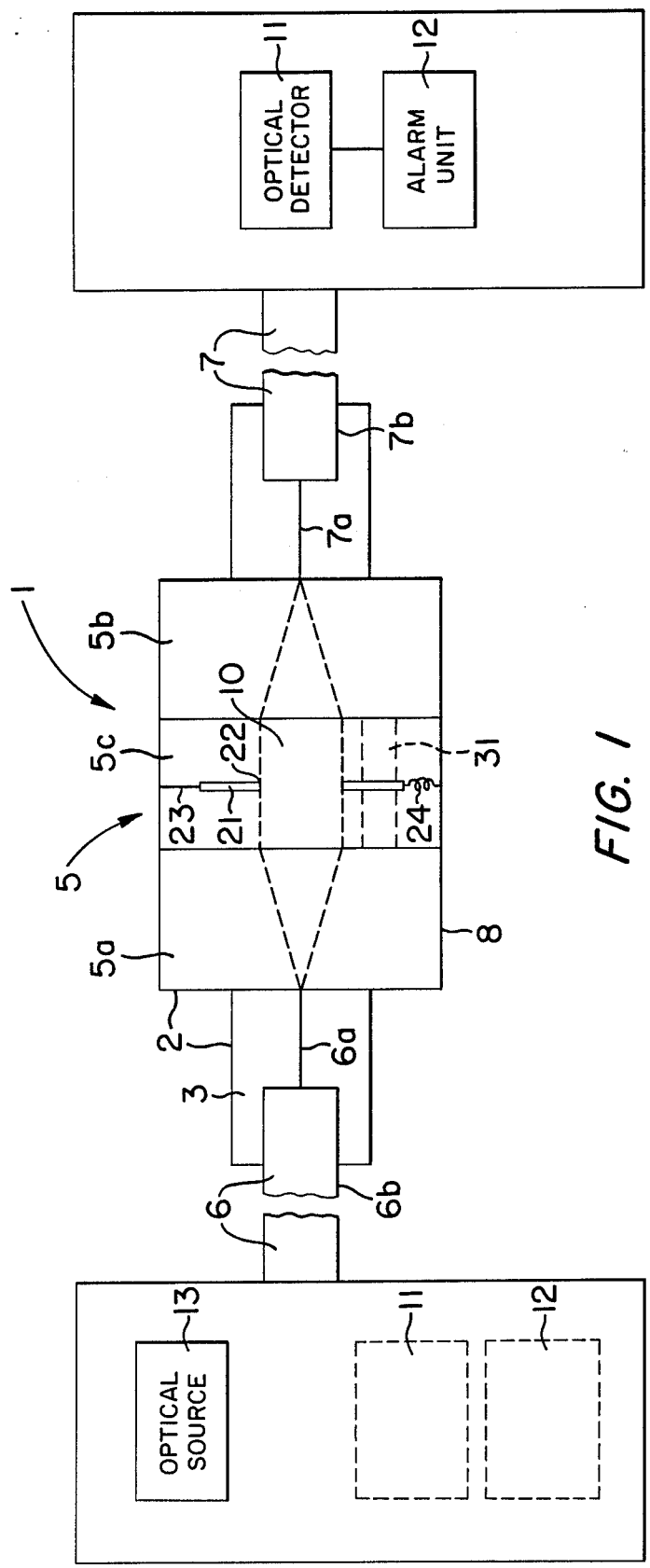
FIG. 1 shows schematically an optical moisture sensor in accordance with the principles of the present invention.

FIG. 1 shows an optical moisture sensor 1 in accordance with the principles of the present invention. The sensor 1 comprises a housing 2 provided with optical coupling ports 3 and 4 which couple optical or light energy to and from an optical assembly 5.

In the illustrated case of FIG. 1, the ports 3 and 4 are each adapted to receive optical fiber cables, shown as cables 6 and 7. The cables 6 and 7 include central optical fibers 6a and 7a which are brought out from the cable casing or sheathing (which includes the fiber cladding) 6b and 7b to a point adjacent the optical assembly 5.

In accordance with the principles of the present invention, the optical assembly 5 includes a beam expander unit 5a which acts to provide an expanded, collimated optical beam 10 from the optical energy or beam coupled to the assembly 5 from the fiber-optic cable 6. Moreover, in further accord with the invention, the assembly 5 is adapted to be responsive to moisture in a way which affects transmission of the expanded beam 10.

In the illustrative case of FIG. 1, the assembly 5 is made responsive to the moisture in the environment of the sensor 1 via apertures 8 in the housing 2. These apertures provide communication between the exterior of the housing and the interior of the housing. In particular, moisture in the exterior environment can travel through the apertures 8 to interact or cloud the beam expander 5a. This, in turn, reduces or attenuates the intensity of the developed expanded, collimated beam 10. As a result, by sensing the intensity of the beam (either directly or indirectly), as by an optical detector, the moisture condition of the exterior environment can be sensed and detected.

As illustrated in FIG. 1, the optical assembly 5 further includes a beam contractor 5b which is spaced from the beam expander 5a by a gap region 5c. The beam contractor 5b receives the portion of the expanded, collimated beam 10 which is transmitted from the expander 5a, after the beam portion traverses the gap 5c. The contractor, in turn, reduces the beam diameter for coupling to the fiber 7a.

Disposed at the end of the cable 7 is an optical detector 11. The detector 11 monitors the intensity of the beam coupled from the cable 7 and thereby the intensity of the associated expanded, collimated beam 10. The monitored intensity is then fed to an alarm unit 12, which gives an alarm condition when the intensity reduces below a set level indicative of an undesired reduction in the beam 10 intensity and a corresponding undesired moisture condition in the environment of the sensor 1.

As an alternative to placing the detector 11 and alarm unit 12 at the end of fiber cable 7, these units may also be placed at the end of the fiber cable 6 as shown in dotted line. In this case, the portion of the expanded, collimated beam 10 which is reflected back through the expander 5a is coupled to these units to provide a measure of the beam intensity. More particularly, this beam portion, on passing back through the assembly 5a is now contracted by the assembly for coupling to the fiber 6a and from the fiber 6a to the detector 11.

The optical energy for the sensor 1 is generated by an optical source 13 which develops an optical beam for entry into the fiber cable 6. Typically, the source 14 can be a laser source which generates a collimated laser beam of very narrow width for passage through the optical fiber 6a of the cable 6.

As described above, beam expander 5a expands optical beams passing in one direction (i.e., from fiber cable 6) through the assembly 5 and contracts beams passing in the opposite direction. The beam contractor 5b acts similarly but for beams in the reverse directions, (i.e., it contracts beams passing through the unit from fiber cable 6 and expands beams passing through from fiber cable 7). The sensor 1 can thus be operated with the optical source 13 at either port with similar results.

The beam expander 5a and beam contractor 5b of the sensor 1 can each, typically, be formed from an aspheric glass lens. Furthermore, the fibers 6a and 7a can typically have diameters of about 7 micron. In such case, the aspheric lens used for the assemblies 5a and 5b might be adapted to provided an expanded beam 10 of about 50 microns.

As can be appreciated, due to the presence of the expanded beam 10, the optical sensor 1 now has a much larger optical area over which moisture can affect the beam and, therefore, the sensor. This significantly improves the sensitivity of the sensor, as does the collimated nature of the expanded beam which enables the sensor to quickly respond to even the slightest moisture presence. The overall configuration of the sensor thus results in a highly sensitive, rapidly responsive unit.

While the moisture responsive nature of the optical sensor 1 as shown in FIG. 1 has been accomplished by apertures 8 which simply allow moisture to impinge upon the expander and contractor 5a and 5b, modifications of this configuration for achieving enhanced moisture responsiveness might also be employed. Thus, for example, an optical shutter 21 having an aperture 22 may be mounted at one end in the gap area 5c by a moisture sensitive element, such as horse hair 23, and at its other end by a spring 24. With this arrangement, the expanded beam, under dry conditions, passes through the aperture 22 undisturbed. However, in the presence of moisture or water, the horse hair 23 becomes stretched, allowing the spring 24 to move the shutter 21 downward, causing blockage and further attenuation of the beam in addition to that caused by clouding of the expander and contractor units. Thus, the attenuation effect of the moisture sensor is enhanced, making subsequent detection of the change in intensity level by detector 11 easier.

Another alternative for increased moisture sensitivity might be to provide between the expander 5a and contractor 5b, a moisture sensitive element 31 which expands or contracts in the presence of moisture, causing tilting of these units. This tilting, like the shutter 21, results in increased attenuation of the expanded beam which again facilitates detection by the detector 11.

Fabrication of the moisture sensor 1 to have features as described hereinabove, can be readily achieved by a simple adaptation of an existing optical fiber connector sold by Lamdek Fiber Optics, a division of Eastman Kodak Company. This connector is described in a publication, dated August 1985, entitled "Design Considerations of the Expanded Beam Lamdek Single-Mode Connector", written by James Carroll, et. al. and distributed by Lamdek Fiber Optics under Publication Part No. LFO-02. In particular, by providing apertures or bores around the circumference of the connector adaptor of this connector, the connector can be made responsive to moisture and, thereby, can be readily transformed into a moisture sensor in accordance with the invention.

Figure 2:
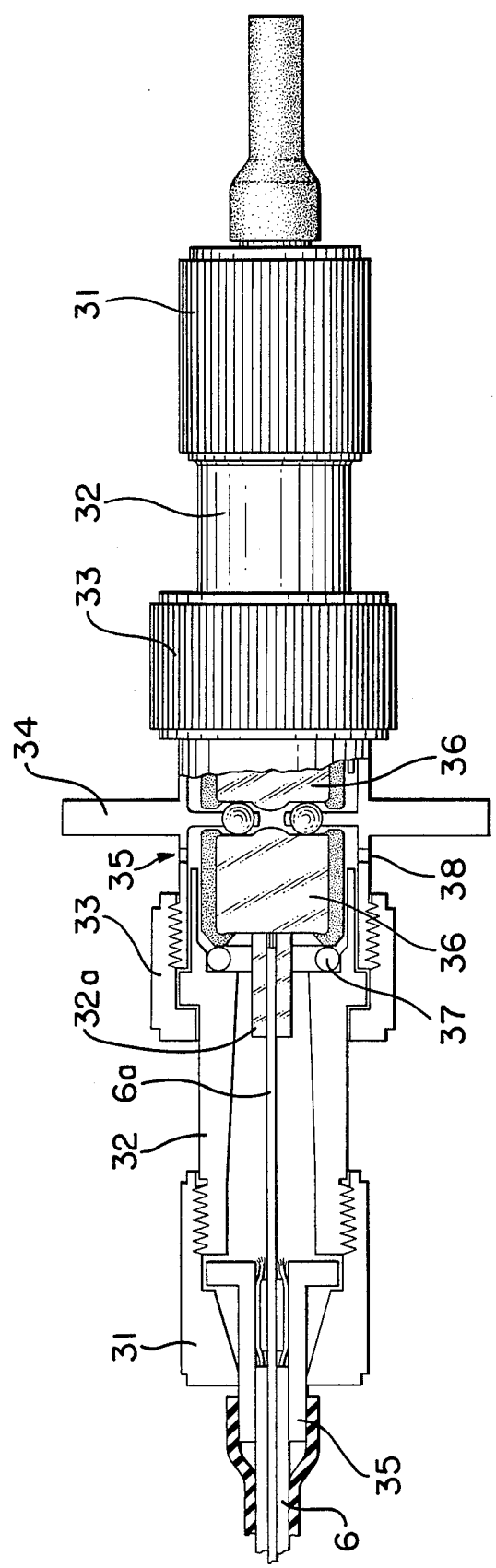
FIG. 2 shows in greater detail a configuration which can be utilized to fabricate the moisture sensor of FIG. 1.

FIG. 2 illustrates pictorially the aforesaid connector adapted in this manner. More particularly, the connector includes end caps 31, plug housings 32, center caps 33 and a connector adaptor 34. The end caps 31 house strain relief members 35 which receive the fiber cables 6 and 7 and through which pass the fibers 6a, 7a to glass ferrules 32a in the plug housings 32. Aspheric lens assemblies 36 situated within the plug housings are centered and aligned by the connector adaptor 34 and compression rings 37. Apertures or bores 38 are provided, in accordance with the invention, in the connector adaptor 34 to allow for passage of moisture to the lenses assemblies 36 so as to result in the desired moisture sensor operation as discussed above.

Figure 3:
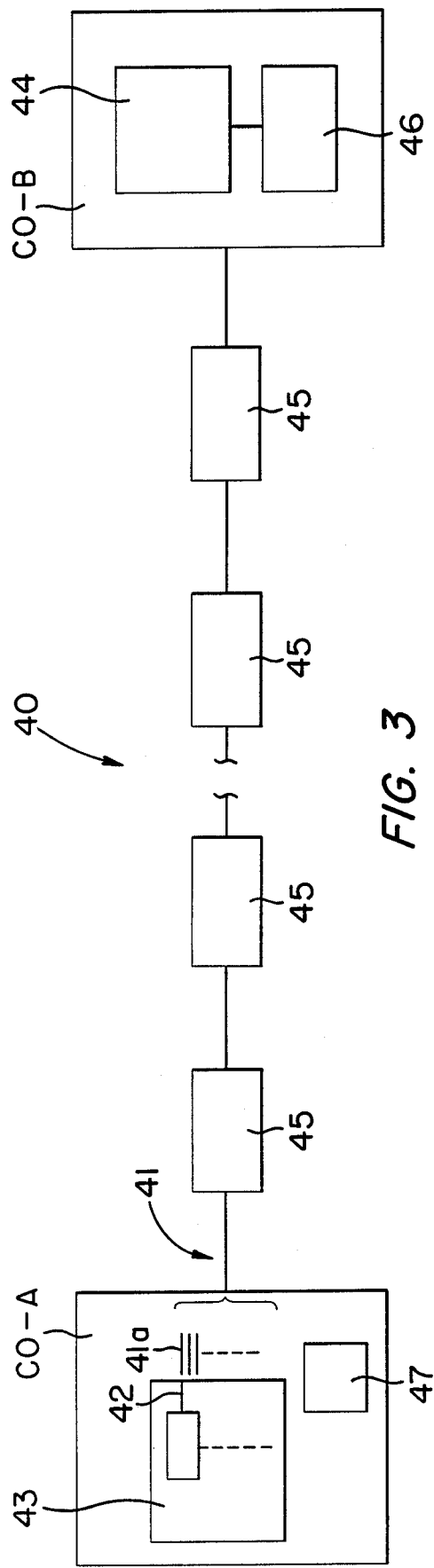
FIG. 3 shows a fiber-optic transmission system in which the sensor of FIGS. 1 and 2 is utilized.

As above-mentioned, the moisture sensor 1 of the invention is particularly useful for sensing the moisture conditions in a fiber optic transmission system such as, for example, a fiber optic transmission system utilized for telephone communications. FIG. 3 illustrates at 40 such a fiber-optic system.

As shown, a fiber optic cable 41 is utilized to provide telephone communication between first and second telephone central offices CO-A and CO-B. The central office CO-A is provided with transmitter equipment 43 for transmitting communication signals over the cable 41 to the central office CO-B. The central office CO-B, in turn, is provided with receiver equipment 44 for receiving the transmitted signals and for monitoring the level of the signals and with an alarm indicator 46 for signalling when the level is below a desired level.

The fiber optical cable 41 is comprised of one or more fiber lines 41a each of which corresponds to an individual communication path or talk channel. Each of the fiber lines, in turn, carries its own laser beam 42 and the detector at the central office CO-B monitors each beam or path individually. Failure of a beam or path then causes a corresponding alarm in alarm indicator unit 46.

Between the central office CO-A and the central office CO-B, the system 40 is provided with one or more locations or stations 45 at which individual fiber lengths forming the respective fiber lines 41a of the fiber cable 41 are joined. These stations 45 may be simple splice stations or repeater stations or any other stations where splicing or joining of individual fiber lengths is necessitated.

Because of the inability to control environmental conditions at the splice stations 45, it is desirable, as above-mentioned, to be able to sense the moisture conditions at these stations, since excessive moisture can have a detrimental effect on the fiber lines and splice components. In accordance with a further aspect of the present invention, a moisture sensor 1 in accordance with the invention, is disposed at each of the splice stations 45.

Figure 4:
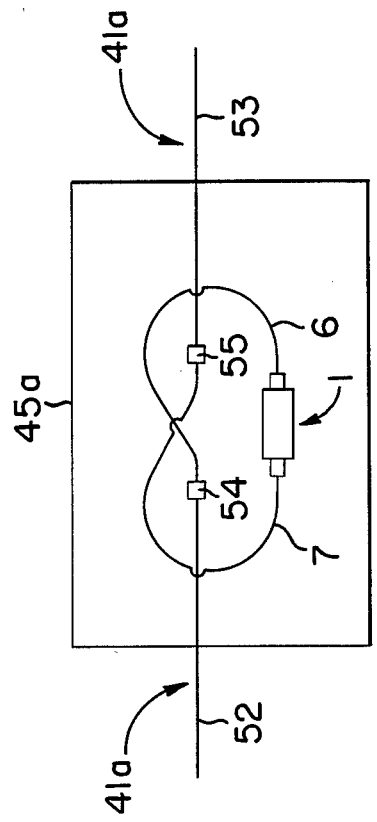
FIG. 4 shows schematically connection of the sensor of FIG. 1 in one of the closures of the system of FIG. 3.

More particularly, FIG. 4, shows utilization of the sensor 1 of the invention in the splice closure 45a of one of the stations 45 of the system 40. As shown, the sensor is disposed in-line between the two fiber lengths 52, 53 of the fiber line 41a. Fiber-optic connectors 54, 55 such as, for example, GTE Elastomeric connectors, connect the fiber lines 6 and 7 of the sensor to the respective fiber lengths 52, 53. With the sensor 1 so disposed, moisture penetration into the closure 45a will result in attenuation of the expanded, collimated laser beam generated in the sensor, as above-described. This attenuation will be detected on the line 41a at the central office CO-B and will result in an alarm indicating a moisture condition.

As above-indicated, a sensor 1 will usually be placed at each of the splice stations 45 in the system 40 and usually within the same line 41a of the fiber optic cable. As a result, an alarm condition at the central office CO-B for the line 41a, as described above, while indicating a moisture condition, will not identify at which splice station 45 the condition exists. In order to isolate the particular splice station, a conventional optical time domain reflectometer (OTDR) 47 can be used at either central office, once an alarm condition is evidenced.

More particularly, an optical time domain reflectometer (OTDR) transmits an optical beam down a fiber optic line and measures tee energy reflected at points along the line. In the present situation, at a splice station 45 where a splice closure 45a has been subjected to moisture, the corresponding sensor 1 provides attenuation of the transmitted laser beam. As a result, the reflected energy from that beam at such splice station will likewise be attenuated. The output trace of the reflectometer will thus be significantly attenuated at this position along the line and will identify the splice station where the moisture condition exists.

It should be pointed out that the particular fiber optic line 41a along which the moisture sensors 1 are placed in the fiber optic system 40 will depend upon the particular application. Since the sensors 1 themselves add loss to the line 41a, if the system is able to withstand this loss, the line 41a can be an already in place line of the system. Thus the normal service line of the system or, more preferably, a protect line for one of the channels of the system can be used. In this case, the detecting and alarming equipment for the moisture condition can be the existing detecting and alarming equipment of the system.

If the system 40 is unable to accomodate the loss attributable to the sensors 1, a spare fiber can be added to the system 40 for the specific purpose of moisture detection. In this case, an additional laser source would have to be included at the transmitter for the spare line and additional detection and alarming equipment would have to be included at the receiver for detecting the optical energy along the spare line.

In all cases, it is understood that the above-identified arrangements are merely illustrative of the many possible specific embodiments which represent applications of the present invention. Numerous and varied other arrangements can readily be devised in accordance with the principles of the present invention without departing from the spirit and scope of the invention.

What is claimed is:

1. Apparatus comprising:
   one or more means each of which for sensing moisture and each comprising:
   a housing having: a port adapted to receive an optical beam; and means for allowing moisture in the environment exterior of said housing to enter said housing;
   and optical means within said housing for providing an expanded optical beam from the optical beam received by said housing through said port, said optical means including means responsive to moisture, including moisture allowed to enter said housing by said allowing means, for affecting said expanded beam.

2. Apparatus in accordance with claim 1 wherein: said expanded beam is collimated.

3. Apparatus in accordance with claim 2 further comprising: means for sensing the effect of said moisture responsive means on said expanded, collimated beam.

4. Apparatus in accordance with claim 3 wherein; said moisture responsive means upon being subjected to moisture attenuates said expanded, collimated beam.

5. Apparatus in accordance with claim 3 further comprising: means for generating said optical beam and conveying said optical beam to said port.

6. Apparatus in accordance with claim 3 wherein: said means for sensing the effect of said moisture responsive means senses a portion of said expanded, collimated beam passing from said optical means.

7. Apparatus in accordance 6 wherein: the sensed portion of said expanded, collimated optical beam is a portion of said expanded, collimated optical beam reflected by said optical means.

8. Apparatus in accordance with claim 6 wherein: the sensed portion of said expanded, collimated optical beam is a portion of said expanded, collimated optical beam transmitted through said optical means.

9. Apparatus in accordance with claim 2 wherein: said means for allowing moisture to enter said housing of said moisture sensing means comprises one or openings through said housing for communication between said environment and the interior of said housing of said moisture sensing means.

10. Apparatus in accordance with claim 9 wherein: said housing of said moisture sensing means is substantially sealed against water entry other than through said means for allowing.

11. Apparatus in accordance with claim 2 wherein: said means for sensing moisture further comprises optical guide means connected to said port.

12. Apparatus in accordance with claim 11 wherein: said optical guide means comprises a fiber-optic cable.

13. Apparatus in accordance with claim 2 wherein: said housing of said moisture sensing means includes a further port; and said optical means contracts said expanded collimated, optical beam and couples said contracted optical beam to said further port.

14. Apparatus in accordance with claim 13 wherein: said means for sensing moisture further comprises: first and second optical guide means connected to said first and second ports, respectively, of said optical 15. Apparatus in accordance with claim 14 wherein: said first and second optical guide means each comprise a fiber-optic cable.

16. Apparatus in accordance with claim 13 wherein said apparatus further comprises:
an optical fiber transmission system including: a transmitter station; a receiver station; one or more splicing stations therebetween; an optical fiber cable connecting said one or more stations, said cable including one or more optical fiber lines each of which comprising individual lengths of optical fiber which connect the successive stations in said system and which are spliced together at said one or more splicing stations to form their respective optical fiber line;
and said one moisture sensing means is disposed at said one splicing station for sensing the moisture at said one splicing station.

17. Apparatus in accordance with claim 16 wherein: said one moisture sensing means is connected inline between the first and second lengths of optical fiber of a given fiber line spliced at said one splicing station.

18. Apparatus in accordance with claim 17 wherein: said port and further ports are joined, respectively, to said first and second lengths of optical fiber.

19. Apparatus in accordance with claim 17 wherein: said given fiber line is an already existing line of said transmission system.

20. Apparatus in accordance with claim 17 wherein: said given fiber line is a spare fiber line of said transmission system.

21. Apparatus in accordance with claim 16 wherein: the number of moisture sensing means is equal to the number of splicing stations;
and each of said moisture sensing means is disposed at a different splicing station for sensing the moisture at that station.

22. Apparatus in accordance with claim 21 wherein: each moisture sensing means is connected in-line between the first and second lengths of optical fiber of a given fiber line being spliced at the associated splicing station.

23. Apparatus in accordance with claim 22 wherein: the given line at each splicing station is the same fiber line of the optical fiber cable.

24. Apparatus in accordance with claim 22 wherein: the moisture sensing means further comprises first and second fiber-optic cables connected to said port and said further port;
and the first fiber-optic cable of a given moisture sensing means is connected to the first length of the given fiber line being spliced at the associated splicing station and the second fiber-optic cable of the given moisture sensing means is connected to the second length of the given fiber line being spliced at the associated splicing station.

25. Apparatus in accordance with claim 13 wherein: said optical means comprises first and second spaced lenses.

26. Apparatus in accordance with claim 25 wherein: said lenses are aspheric lenses.

* * * * *

UNITED STATES PATENT AND TRADEMARK OFFICE
CERTIFICATE OF CORRECTION

PATENT NO. : 4,866,265
DATED : September 12, 1989
INVENTOR(S) : Harold Hohne

It is certified that error appears in the above-identified patent and that said Letters Patent is hereby corrected as shown below:

Col. 3, line 11. Change "changing" to -- change --
    Col. 3, lines 13, 14 and 15. Change "realizeable" to -- realizable --
    Col. 6, line 18. Change "tee" to -- the --
    Col. 6, line 40. Change "accomodate" to --accommodate--
    Col. 7, line 22. Claim 7. After "accordance" insert -- with claim --
    Col. 7, line 34. Claim 9. After "or" insert -- more --
    Col. 7, line 57. Claim 14. After "optical" insert -- means. --

Signed and Sealed this

Twenty-first Day of August, 1990

*Attest:*

HARRY F. MANBECK, JR.

*Attesting Officer*    *Commissioner of Patents and Trademarks*